United States Patent [19]
Rody et al.

[11] 4,001,266
[45] Jan. 4, 1977

[54] PROCESS FOR THE MANUFACTURE OF 2-(2-HYDROXYPHENYL)BENZTRIAZOLES

[75] Inventors: Jean Rody, Basel; Alain Claude Rochat, Birsfelden, both of Switzerland

[73] Assignee: Ciba-Geigy Corporation, Ardsley, N.Y.

[22] Filed: Nov. 25, 1974

[21] Appl. No.: 527,180

[30] Foreign Application Priority Data

Nov. 27, 1973 Switzerland .................... 16636/73

[52] U.S. Cl. ......................................... 260/308 B
[51] Int. Cl.² ..................................... C07D 249/20
[58] Field of Search ............................... 260/308 B

[56] References Cited

UNITED STATES PATENTS

| | | | |
|---|---|---|---|
| 3,230,194 | 1/1966 | Boyle | 260/308 B |
| 3,773,751 | 11/1973 | Brooks | 260/308 B |

OTHER PUBLICATIONS

Ochiai, "Aromatic Amine Oxides" pub. by Elsevier Pub. Co., Amsterdam, (1967), p. 205.

*Primary Examiner*—Paul M. Coughlan, Jr.
*Attorney, Agent, or Firm*—Luther A. R. Hall

[57] ABSTRACT

Process for the manufacture of 2-(2-hydroxyphenyl)-benztriazoles of the formula I

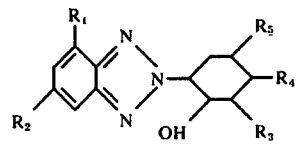

(I)

wherein $R_1$ denotes hydrogen or halogen, $R_2$ denotes hydrogen, alkyl, alkoxy, alkylsulphonyl, acylamino, —$SO_3H$, —COOH or halogen, $R_3$ denotes hydrogen, alkyl, cycloalkyl, aralkyl, aryl or halogen, $R_4$ denotes hydrogen, alkyl, alkoxy or —OH and $R_5$ denotes hydrogen, alkyl, cycloalkyl, aralkyl, aryl, carboxyalkyl, alkoxy, acylamino or halogen, characterized in that a 2-(2-hydroxyphenyl)-benztriazole-1 oxide in the formula III

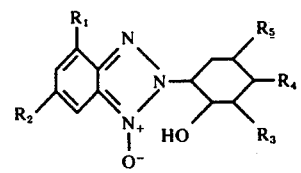

(III)

is reacted with 0.5 to 0.6 mol equivalent of hydrazine hydrate at a temperature above 100° C, in a high-boiling ether as the solvent and in the presence of a base.

9 Claims, No Drawings

PROCESS FOR THE MANUFACTURE OF 2-(2-HYDROXYPHENYL)BENZTRIAZOLES

The present invention relates to a process for the manufacture of 2-(2-hydroxyphenyl)benztriazoles of the formula I

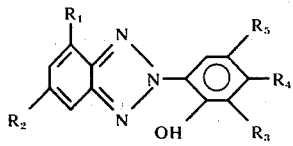

wherein $R_1$ denotes hydrogen or halogen, $R_2$ denotes hydrogen, alkyl, alkoxy, alkylsulphonyl, acylamino, $-SO_3H$, $-COOH$ or halogen, $R_3$ denotes hydrogen, alkyl, cycloalkyl, aralkyl, aryl or halogen, $R_4$ denotes hydrogen, alkyl, alkoxy or $-OH$, and $R_5$ denotes hydrogen, alkyl, cycloalkyl, aralkyl, aryl, carboxyalkyl, alkoxy, acylamino or halogen, characterized in that a 2-(2-hydroxyphenyl)-benztriazole-1 oxide of the formula III

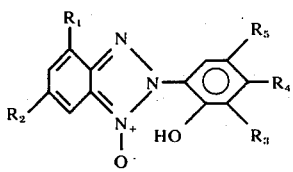

is reacted with 0.5 to 0.6 mole equivalent of hydrazine hydrate at a temperature above 100° C, in a high-boiling ether as the solvent and in the presence of a base.

One can preferably here use the compound of the formula III in the form of a product which has been obtained by reducing a 2-nitro-2'-hydroxyazobenzene of the formula II

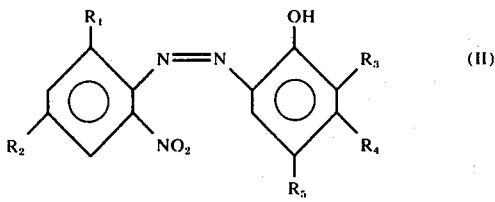

with hydrazine hydrate.

It is already known to reduce 2-nitro-2'-hydroxyazobenzenes to 2-(2-hydroxyphenyl)benztriazoles. For this purpose it is customary to use metals, above all zinc, which are obtained as metal oxides after the reaction. The removal of these oxides requires a considerable effort, since large quantities are involved, which must be removed from the equipment and must subsequently be transported away and worked up in order to regenerate the metal. Moreover, metal oxides remain dissolved in the effluent, which, in addition, poses expensive problems of environmental protection. Other reducing agents which are employed are alkali metal sulphides and trialkyl phosphites, but they are inferior to the metals.

It is, furthermore, known that the triazole oxides formed as intermediate products in the manufacture of the 2-(2-hydroxyphenyl)benztriazoles can be reduced to the corresponding benztriazoles with relative difficulty, regardless of whether the intermediate products are isolated or the attempt is made to reduce at once to the benztriazole in one stage. Besides the abovementioned reducing agents, hydrazine hydrate is also suitable for overcoming these difficulties in the case of some N-oxides of aromatic heterocyclic compounds or in the case of some reactions which proceed via such N-oxides. If this reducing agent is used in the presence of metals, such as, for example, nickel as a catalyst, ammonia is produced as a byproduct in large amounts. That is to say, a large excess of hydrazine hydrate has to be employed. Since it is additionally necessary to work up the catalyst after the reaction, this process is uneconomic for the manufacture of 2-(2-hydroxyphenyl)-benztriazoles. The few known reductions of N-oxides of aromatic heterocyclic compounds using hydrazine hydrate without a catalyst give poor yields of the desired reduction product, even if a large excess of the reducing agent is employed.

In the search for an economic process, without environmental problems, it has been found, surprisingly, that the difficult reduction of benztriazole-1 oxides takes place with a very good yield, even without a metallic catalyst, using hydrazine hydrate alone.

This reaction has the great advantage that, even on an industrial scale, almost stoichiometric quantities of hydrazine hydrate are adequate for the reduction and, apart from the desired 2-(2-hydroxyphenyl)benztriazole, virtually the only byproducts produced are water and nitrogen, which do not contaminate the effluent.

In the process according to the invention, the supply of the reactants to the reaction vessel and the removal of the reaction products is a simple matter.

The new reduction is just as economic or even more economic than the reduction by means of metals, without producing problems of environmental pollution.

Compounds of the formula I which are preferentially manufactured by the process according to the invention are those in which $R_1$ denotes hydrogen, chlorine or bromine, $R_2$ denotes hydrogen, alkyl having 1 to 8 carbon atoms, alkoxy having 1 to 12 carbon atoms, alkylsulphonyl having 1 to 12 carbon atoms, acylamino having 2 to 12 carbon atoms, $-SO_3H$, $-COOH$, bromine or chlorine, $R_3$ denotes hydrogen, alkyl having 1 to 12 carbon atoms, cycloalkyl having 6–8 carbon atoms, aralkyl having 7 to 11 carbon atoms, phenyl, chlorine or bromine, $R_4$ denotes hydrogen, methyl, alkoxy having 1 to 12 carbon atoms, or OH, and $R_5$ denotes hydrogen, alkyl having 1 to 12 carbon atoms, cycloalkyl having 6 to 8 carbon atoms, aralkyl having 7 to 11 carbon atoms, phenyl, carboxyalkyl having 2 to 13 carbon atoms, alkoxy having 1 to 12 carbon atoms, acylamino having 2 to 12 carbon atoms, chlorine or bromine.

If $R_2$, $R_3$, $R_4$ or $R_5$ are defined as alkyl, they are, for example, methyl, ethyl, n-propyl, iso-propyl, n-butyl, iso-butyl, tert.-butyl, n-pentyl, iso-pentyl, tert.-amyl, hexyl, n-octyl, iso-octyl or tert.-octyl.

If $R_3$ or $R_5$ denote aryl, they can be phenyl.

If $R_3$ or $R_5$ are aralkyl, they are, for example, benzyl, α-methylbenzyl, α,α-dimethylbenzyl or naphthyl-1-methyl.

If $R_3$ or $R_5$ denote cycloalkyl, they can be cyclohexyl, α-methylcyclohexyl or cyclooctyl. If $R_2$ or $R_5$ denote acylamino, they can be, for example, acetyl-, propionyl-, butyroyl-, pentanoyl- 2-ethylhexanoyl-, lauroyl-, benzoyl-, phenylacetyl-, acryloyl-, methacryloyl- or cyclohexylcarbonylamino.

If $R_5$ denotes carboxyalkyl, it can be carboxymethyl or carboxyethyl.

If $R_2$, $R_4$ or $R_5$ denote alkoxy, they can be, for example, methoxy, ethoxy, propoxy, butoxy, β-methoxyethoxy, pentyloxy, iso-butoxy, octoxy or dodecyloxy.

If $R_2$ is alkylsulphonyl, it can be methylsulphonyl, ethylsulphonyl, butylsulphonyl or octylsulphonyl.

In the meaning of halogen, $R_1$, $R_2$, $R_3$ or $R_5$ can denote chlorine or bromine.

Examples of compounds of the formula I are: 2-(2-hydroxy-5-methylphenyl)benztriazole, 2-(2-hydroxy-5-tert.butylphenyl)benztriazole, 2-(2-hydroxy-5-tert.-octylphenyl)benztriazole, 2-(2-hydroxy-3-tert.butyl-5-methylphenyl)benztriazole, 2-(2-hydroxy-3-tert.butyl-5-methylphenyl)-5-chloro-benztriazole, 2-(2-hydroxy-3,5-ditert.butylphenyl)benztriazole, 2-(2-hydroxy-3,5-di-tert.butylphenyl)-5-chloro-benztriazole, 2-(2-hydroxy-3,5-di-tert.-amylphenyl)benztriazole, 2-(2-hydroxy-3,5-di-tert.amylphenyl)-5-chloro-benztriazole, 2-(2-hydroxy-3-sec.butyl-5-tert.-butyl-phenyl)benztriazole, 2-(2-hydroxy-3-tert.butyl-5-sec.-butyl-phenyl)benztriazole, 2-(2,4-dihydroxyphenyl)-benztriazole, 2-(2-hydroxy-4-methoxyphenyl)benztriazole, 2-(2-hydroxy-4-octoxyphenyl)benztriazole, 2-(2-hydroxy-3-α-phenylethyl-5-methylphenyl)-benztriazole and 2-(2-hydroxy-3α-phenylethyl-5-methylphenyl)-5-chloro-benztriazole.

The process according to the invention is carried out in high-boiling ethers, preferably having a boiling point of at least 140° C, such as, for example, phenyl methyl ether, phenyl ethyl ether, diphenyl ether, ethylene glycol dibutyl ether, diethylene gylcol dimethyl ether, diethylene glycol diethyl ether, diethylene glycol dibutyl ether, triethylene glycol dimethyl ether, tetraethylene glycol dimethyl ether and the like. Preferably, diethylene glycol dimethyl ether and diethylene glycol diethyl ether are used. Examples of bases used in the process according to the invention are alkali metal hydroxides, such as sodium hydroxide or potassium hydroxide. The reduction according to the invention takes place above 100° C, preferably at 100° to 180° C, and particularly preferentially at 120° to 150° C. The compounds of the formula I can be prepared by the process according to the invention, not only from the compounds of the formula III, but also direct from the compounds of the formula II without isolating an intermediate product. In the last process variant, a compound of the formula II, dissolved in a high-boiling ether, is (a) reduced to a compound of the formula III by adding 0.5 mol equivalent of hydrazine hydrate in the presence of a base at 70° to 100° C, preferably at 80° to 90° C. The duration of addition of the hydrazine hydrate varies between a few seconds and a few hours, it is normally ½ to 3 hours. The water present is then removed by azeotropic distillation together with part of the ether, until a temperature of more than 100° C, preferably 100° to 180° C and particularly preferentially 120° to 150° C, is reached in the reaction mixture.

Subsequently, (b) a further 0.5 to 0.6 mol equivalent of hydrazine hydrate is added at a uniform rate over the course of 1 to 5 hours in order to reduce the compound of the formula III present in the solution or suspension. The water which is formed in the course thereof is continuously removed azeotropically together with part of the solvent, in order to keep the reaction temperature above 100° C, preferably at 100° to 180° C and particularly preferentially at 120° to 150° C.

If a compound of the formula III is used as starting material in the process according to the invention, the process is carried out only as described under (b).

The compounds of the formula I are stabilisers for organic materials, such as, for example, organic polymers. Their use is described in French Patent Application No. 1,195,307.

The preparation of the azobenzenes of the formula II or the 2-(2-hydroxyphenyl)benztriazole-1 oxides of the formula III, which are used as the starting compound, is described in U.S. Pat. Nos. 3,230,194 and 3,076,782.

The invention is described in greater detail in the following examples.

EXAMPLE 1

156 g (0.4 mol) of 2-nitro-4-chloro-2'-hydroxy-3',5'-ditert.-butylazobenzene and 50.7 g (0.38 mol) of 30% strength sodium hydroxide solution are introduced into 360 ml of diethylene glycol diethyl ether and the mixture is heated to 85° C. 10.5 g (0.21 mol) of hydrazine hydrate are added at a uniform rate to the mixture over the course of 90 minutes, while holding the temperature constant. After the addition is complete, the mixture is heated to 90° C and is kept at this temperature for about 1 hour. An azeotropic mixture of water and solvent is then distilled off from this solution until a temperature of 132° C is reached in the reaction mixture. 11.25 g (0.225 mol) of hydrazine hydrate are then added over the course of 112 minutes, the temperature being kept at 130° to 132° C by distilling off an azeotropic mixture of water and solvent.

After the addition is complete, the mixture is left for about 30–60 minutes at 132° C to complete the reaction, until the evolution of nitrogen stops completely and the distillation dies away. The resulting reaction solution is then cooled to 90° C while being flushed with nitrogen, approx. 13.9 g of hydrogen chloride gas are passed in in order to neutralize the mixture completely, 6 g of a decolorizing agent are added, the mixture is stirred for approx. 30 minutes at 90° C and the resulting suspension is clarified through a pressure filter using nitrogen. The resulting solution is allowed to cool to 0° C and the precipitated product is filtered off, washed and dried. 120.5 g of pure 2-(2'-hydroxy-3',5'-ditert.-butylphenyl)-5-chlorobenztriazole are obtained. About 8.5 g of product can be obtained additionally from the mother liquor, which corresponds to a total yield of 90% of theory (relative to the azeobenzene derivative employed).

EXAMPLE 2

152 g (0.4 mol) of 2-(2-hydroxy-3-α-phenylethyl-5-methylphenyl)-6-chloro-benztriazole-1 oxide and 17.6 g (0.44 mol) of sodium hydroxide are introduced into 327 g of diethylene glycol dimethyl ether and the mixture is heated to 130° C, a little water distilling off azeotropically with the solvent. Exactly 12.0 g (0.24 mol) of hydrazine hydrate are passed in under the surface of the solution over the course of 1½ hours while keeping the temperature between 133° and 135° C. In the course thereof, the water liberated is continuously removed by azeotropic distillation. After the addition is complete, the mixture is left to complete the reaction for about 1 hour at the same temperature and, as soon as the evolution of nitrogen stops, the resulting solution is cooled to 80° C and treated with 200 ml of cold water. About 53.7 g of 30% strength hydrochloric acid are then added dropwise at a regular rate until the mixture has a neutral reaction and it is cooled to about 40° C while stirring vigorously, whereupon the product crystallises out. The suspension is then diluted with 800 ml of water and filtered and the crude product is washed with a total of 300 ml of hot water. After drying in vacuo at 60°–70° C, 137.5 g of 2-(2-hydroxy-3-α-phenylethyl-5-methylphenyl)-5-chloro-benztriazole of 97% purity are obtained, which corresponds to a yield of 91.5% of theory. The melting point is 113°–115° C (the pure product melts between 115° and 119° C).

EXAMPLE 3

A mixture of 290 g of diethylene glycol dimethyl ether, 4.5 g (0.08 mol) of potassium hydroxide and 133.5 g (0.39 mol) of 97% strength 2-(2'-hydroxy-3'-tert.butyl-5'-methylphenyl)-6-chloro-benztriazole-1 oxide is heated to 135° C. 12.0 g (0.24 mol) of hydrazine hydrate are run into the mixture at a regular rate over the course of 3 hours and the water liberated is continuously removed by azeotropic distillation at 134°–136° C. At the conclusion of the addition of hydrazine, the resulting solution is thoroughly stirred for a further 15–45 minutes at 134°–136° C, until the evolution of nitrogen stops completely. The mixture is then cooled to 90° C and 200 ml of water and approx. 19 g of 30% strength hydrochloric acid are added. The resulting suspension is diluted with 1.3 liters of warm water, stirred briefly at 70°–80° C and filtered on a suction filter. After one wash with about 200 ml of hot water the product is dried in vacuo at 60°–70° C. This gives 125 g of 92% strength 2-(2'-hydroxy-3'-tert.butyl-5'-methylphenyl)-5-chloro-benztriazole, which corresponds to a yield of 93.5% of theory.

What we claim is:

1. A process for the manufacture of a 2-(2-hydroxyphenyl)-benzotriazole of the formula I

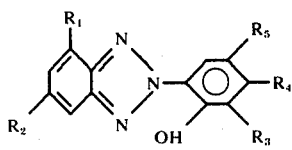

wherein $R_1$ denotes hydrogen, chlorine or bromine, $R_2$ denotes hydrogen, alkyl having 1 to 8 carbon atoms, alkoxy having 1 to 12 carbon atoms, alkylsulphonyl having 1 to 12 carbon atoms, acylamino having 2 to 12 carbon atoms, $—SO_3H$, $—COOH$, bromine or chlorine, $R_3$ denotes hydrogen, alkyl having 1 to 12 carbon atoms, cycloalkyl having 6 to 8 carbon atoms, aralkyl having 7 to 11 carbon atoms, phenyl, chlorine or bromine, $R_4$ denotes hydrogen, methyl, alkoxy having 1 to 12 carbon atoms, or OH, and $R_5$ denotes hydrogen, alkyl having 1 to 12 carbon atoms, cycloalkyl having 6 to 8 carbon atoms, aralkyl having 7 to 11 carbon atoms, phenyl, carboxyalkyl having 2 to 13 carbon atoms, alkoxy having 1 to 12 carbon atoms, acylamino having 2 to 12 carbon atoms, chlorine or bromine, which comprises reacting in a molar ratio 1 mole of a 2-(2-hydroxyphenyl)benzotriazole-1-oxide of formula III

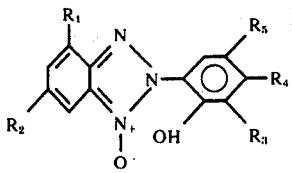

with 0.5 to 0.6 moles of hydrazine hydrate in the presence of a base and at a temperature above 100° C in an ether solvent with a boiling point over 140° C and selected from the group consisting of phenyl methyl ether, phenyl ethyl ether, diphenyl ether, ethylene glycol dibutyl ether, diethylene glycol dimethyl ether, diethylene glycol diethyl ether, diethylene glycol dibutyl ether, triethylene glycol dimethyl ether, and tetraethylene glycol dimethyl ether, and removing the water formed by azeotropic distillation.

2. A process according to claim 1 wherein the ether solvent is diethylene glycol dimethyl ether or diethylene glycol diethyl ether.

3. A process according to claim 1 wherein the temperature is maintained between 100° and 180° C.

4. A process according to claim 3 wherein the temperature is maintained between 120° and 150° C.

5. A process for the manufacture of a 2-(2-hydroxyphenyl)-benzotriazole of the formula I

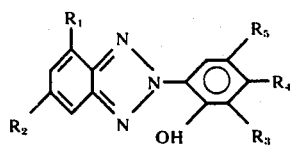

wherein $R_1$ denotes hydrogen, chlorine or bromine, $R_2$ denotes hydrogen, alkyl having 1 to 8 carbon atoms, alkoxy having 1 to 12 carbon atoms, alkylsulphonyl having 1 to 12 carbon atoms, acylamino having 2 to 12 carbon atoms, $—SO_3H$, $—COOH$, bromine or chlorine, $R_3$ denotes hydrogen, alkyl having 1 to 12 carbon atoms, cycloalkyl having 6 to 8 carbon atoms, aralkyl having 7 to 11 carbon atoms, phenyl, chlorine or bromine, $R_4$ denotes hydrogen, methyl, alkoxy having 1 to 12 carbon atoms, or OH, and $R_5$ denotes hydrogen, alkyl having 1 to 12 carbon atoms, cycloalkyl having 6 to 8 carbon atoms, aralkyl having 7 to 11 carbon atoms, phenyl, carboxyalkyl having 2 to 13 carbon atoms, alkoxy having 1 to 12 carbon atoms, acylamino having 2 to 12 carbon atoms, chlorine or bromine, which comprises first reducing in a molar ratio 1 mole of a 2-nitro-2'-hydroxyazobenzene of formula II

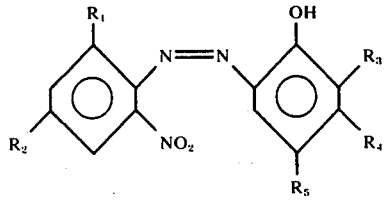

with 0.5 moles of hydrazine hydrate in the presence of a base and at a temperature between 70° C and 100° C in an ether solvent having a boiling point over 140° C and selected from the group consisting of phenyl methyl ether, phenyl ethyl ether, diphenyl ether, ethylene glycol dibutyl ether, diethylene glycol dimethyl ether, diethylene glycol diethyl ether, diethylene glycol dibutyl ether, triethylene glycol dimethyl ether and tetraethylene glycol dimethyl ether to form a 2-(2-hydroxyphenyl)benzotriazole-1-oxide of formula III

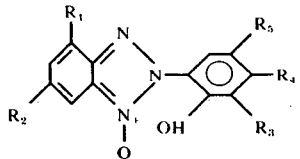

removing the water formed by azetropic distillation and raising the temperature of the reaction mixture to over 100° C, and addind an additional 0.5 to 0.6 moles of hydrazine hydrate to complete at a temperature over 100° C the reduction of the compound of formula III to the desired product of formula I concomitantly removing the water formed by azeotropic distillation.

6. A process according to claim 5 wherein the ether solvent is diethylene glycol dimethyl ether or diethylene glycol diethyl ether.

7. A process according to claim 5 wherein the temperature of the reduction reaction of a compound of formula II to a compound of formula III is maintained at 80° to 90° C.

8. A process according to claim 5 wherein the temperature of the reaction mixture is maintained during the reduction of a compound of formula III to the product of formula I between 100° and 180° C.

9. A process according to claim 8 wherein the temperature is maintained between 120° and 150° C.

* * * * *